United States Patent

Dralle-Voss et al.

[11] Patent Number: 6,096,911
[45] Date of Patent: Aug. 1, 2000

[54] PROCESS FOR PURIFYING ALKOXYLATED FATS

[75] Inventors: Gabriele Dralle-Voss, Alsbach-Hähnlein; Michael Stösser, Neuhofen; Siegfried Lang, Ludwigshafen; Thomas Saupe, Sandhausen; Matthias Zipplies, Neustadt, all of Germany

[73] Assignee: BASF Aktiengesellschaft, Ludwigshafen, Germany

[21] Appl. No.: 09/043,502

[22] PCT Filed: Sep. 20, 1996

[86] PCT No.: PCT/EP96/04116

§ 371 Date: Mar. 24, 1998

§ 102(e) Date: Mar. 24, 1998

[87] PCT Pub. No.: WO97/12017

PCT Pub. Date: Apr. 3, 1997

[30] Foreign Application Priority Data

Sep. 28, 1995 [DE] Germany ............ 195 36 165

[51] Int. Cl.$^7$ ...................................... C11B 3/10
[52] U.S. Cl. ............ 554/191; 554/193; 554/198; 554/202
[58] Field of Search ................. 554/149, 143, 554/198, 202, 191

[56] References Cited

U.S. PATENT DOCUMENTS

| 4,735,815 | 4/1988 | Taylor et al. | 426/417 |
| 5,504,102 | 4/1996 | Agharkar et al. | 514/449 |

FOREIGN PATENT DOCUMENTS

| 645 145 | 3/1995 | European Pat. Off. |
| 256 631 | 2/1999 | European Pat. Off. |
| 94/12030 | 6/1994 | WIPO |

OTHER PUBLICATIONS

JP 58020152—Derwent Abst, 1983.
JP 1099518—Derwent Abst, 1989.

*Primary Examiner*—Deborah D. Carr
*Attorney, Agent, or Firm*—Keil & Weinkauf

[57] ABSTRACT

A process for purifying alkoxylated fats by treatment with a solid substance, wherein a mixture of aluminum oxide and a silicate is employed as solid substance.

9 Claims, No Drawings

PROCESS FOR PURIFYING ALKOXYLATED FATS

This application is a 371 of PCT/CP96/04116 filed Sep. 20, 1996.

BACKGROUND OF THE INVENTION

The invention relates to a process for purifying alkoxylated fats by treatment with a solid substance, to alkoxylated fats obtainable by this process, and to the use thereof.

Alkoxylated fats are employed for a large number of purposes. One purpose, which is increasing in importance, is the use as constituent of the solvent for preparing solutions of active substances which are insoluble in water, especially drugs. For administration of drugs it is necessary in certain cases that the drugs are present in stable solutions, eg. when the drugs are to be infused.

EP 645 145 A discloses pharmaceutical formulations which consist of a solution of an antineoplastic active substance and of a solvent, with the solvent comprising alkoxylated fats as cosolvent or solubilizer. The pharmaceutical formulation is stabilized by addition of an acid or of a salt or by treatment of the alkoxylated fat with aluminum oxide, in particular owing to the fact that the carboxylate content is reduced to a particular level.

WO 94/12030 discloses that pharmaceutical formulations as described in EP 645 145 can be stabilized by adding particular acids, in which case the resulting pH must be below 8.1.

However, these prior art constituents of pharmaceutical formulations often do not yet meet the requirements to be met by such constituents in respect of the stability of the resulting formulation.

BRIEF SUMMARY OF THE INVENTION

It is an object of the present invention to provide a process with which alkoxylated fats can be purified so that they are more suitable for use in pharmaceutical formulations.

We have found that this object is achieved by a process for purifying alkoxylated fats by treatment with a solid substance, wherein a mixture of aluminum oxide and a silicate is employed as solid substance.

Not only is it possible with the process according to the invention to reduce the content of impurities, it is also possible to diminish the water content and lower the pH.

Surprisingly, the process according to the invention also reducers the viscosity of the alkoxylated fat, which results in products which can be administered better. If the viscosities of the starting material are in the range 700–850 mPa·s, the product purified according to the invention has a viscosity in the range 600–750 mPa·s, ie. a reduction of 100 mPa·s in each case. In addition, a reduction in catalyst residues can also be achieved.

DETAILED DESCRIPTION OF THE INVENTION

A preferred embodiment of the process according to the invention comprises mixing and stirring the alkoxylated fats with the aluminum oxide and the silicate (adsorbents) and then filtering off the solid substances. It was surprising that the desired purifying effect is achieved simply by mixing the components, where appropriate at elevated temperature. The treatment of the alkoxylated fat preferably takes place by mixing with the adsorbents and stirring at 15–180° C., preferably at 30–100° C., in particular 40–80° C. The pressure can be reduced to 10–800 mbar during the reaction. The reaction can also be carried out under protective gas (eg. $N_2$). The reaction time is preferably from 1 to 12 h. 0.5–15% by weight, in particular 1–10% by weight, of adsorbents are preferably added. It is also possible additionally for 0–3% by weight of a filtration aid, such as diatomaceous earth (kieselguhr), to be added.

The silicates preferably employed are alkali metal and/or alkaline earth metal silicates, especially Mg silicate or Ca silicate, or Al silicates, but also fuller's earth. Commercial products which may be mentioned by way of example are Ambosol, Tonsil FF or Magnesol.

The mixture of aluminum oxide and silicate is, as a rule, obtained by mechanically mixing the two constituents, eg. in the reaction vessel.

A preferred embodiment of the process furthermore comprises adding an acid before, during or after the treatment with the solid substances. The purified final product can be acidified, for example with short-chain (1–3 carbon atoms) organic acids, eg. acetic acid, to a pH <7. However, other acids such as citric acid or mineral acids are also suitable. EP 645 145 indicates the possible acids. Furthermore, acidic salts such as the ammonium salt of amino acids, eg. glycine hydrochloride, can also be employed for the acidification.

The present invention also relates to purified alkoxylated fats which have been prepared by the process according to the invention, and to the use of the alkoxylated fats prepared according to the invention for the production of pharmaceutical formulations.

Alkoxylated fats purified by the process according to the invention are, for example, ethoxylated fatty acids, especially ethoxylated castor oil, as sold by the applicant under the proprietary name Cremophor® EL. However, other fats as mentioned in EP 645 145 A and its equivalent U.S. Pat. No. 5,504,102 can also be purified by the process according to the invention.

Pharmaceutical formulations produced with the alkoxylated fats which have been purified according to the invention and, where appropriate, acidified are, in particular, those containing active substances which are insoluble in water. The formulations also comprise as a rule another solvent constituent such as an alcohol, especially ethanol, in which case the ratio of alkoxylated fat to alcohol can be 30:70–70:30.

The intended active substances are, in particular, active substances which are insoluble in water, especially antineoplastic active substances such as paclitaxel (Taxol®). Concerning other possible active substances (such as teniposide, camptothecin and derivatives thereof), express reference is made to EP 645 145 A.

EXAMPLES

Example 1

An ethoxylated castor oil (Cremophor® EL) with the following analytical data was employed:

pH 7.0 viscosity: 750 mPa·s

Karl-Fischer water content about 2.5% free fatty acid content 0.1–0.5%

2500 kg of 100 % pure Cremophor® EL were heated to 50° C. under $N_2$, and 75 kg of magnesium silicate (Ambosol 500 from Hoechst), 75 kg of acidic aluminum oxide and 5.25 kg of diatomaceous earth (Hyflow from Lehmann & Voss= kieselguhr filtration aid (flow-calcined white freshwater diatoms)) were added. The mixture was stirred at 50–55° for 3.5 h. The adsorbents were then filtered off. The pore size of the filter was from 10 μm to 20 μm.

Example 2

The process was that of Example 1 but a basic Al oxide was employed in place of the acidic Al oxide.
Results:

|   | Adsorbent | $H_2O$ content % | Free fatty acid content % |
|---|---|---|---|
| 1 | 3% magnesium silicate/ 3% acidic aluminum oxide[1)] | 0.15 | 0.03 |
| 2 | 5% magensium [sic] silicate/[2)] 5% basic aluminum oxide | 0.49 | 0.02 |

[1)]Aluminum oxide 90 active, acidic, Merck activity level 1
[2)]$Al_2O_3$ W 200 strongly basic The pH of the product obtained in Example 1 was 5.9, ie. a stabilizing effect is achieved owing to the reduction in the pH even without additional acidification (pH measured in 10% strength aqueous solution.)

The viscosity was 650 mPa·S

For comparison, the following tests were carried out:

|   | Adsorbent | $H_2O$ content % | Fatty acid content % |
|---|---|---|---|
| 3 | 3% magnesium [sic] silicate | 0.69 | 0.11 |
| 4 | 5% magnesium silicate | 0.16 | 0.11 |
| 5 | 3% acidic Al oxide[1] | 0.24 | 0.06 |

[1]Aluminum oxide 90 active, acidic, Merck activity level 1

The results show that on use of aluminum oxide or silicate each on its own the desired results, especially the low fatty acid content, are not achieved. However, the use, according to the invention, of the adsorbents together leads in a surprising manner to a synergistic effect, so that the resulting product is advantgeously suitable for pharmaceutical formulations.

We claim:

1. A process for purifying ethoxylated fatty acids for the production of pharmaceutical formulations by treatment with a solid substance, wherein a mixture of aluminum oxide and a silicate is employed as solid substance and then filtering off the solid substances.

2. A process as claimed in claim 1, wherein the treatment is carried out at 15–180° C.

3. A process as claimed in claim 1, wherein an alkali metal or/and alkaline earth metal silicate is used as silicate.

4. A process as claimed in claim 1, wherein the treatment comprises mixing and stirring the ethoxylated fatty acids with the aluminum oxide and the silicate, and subsequently filtering off the solid substances.

5. A process as claimed in claim 4, wherein from 0.5 to 15% by weight of the solid substances, based on the complete mixture, are employed.

6. A process as claimed in claim 4, wherein additionally 0–2% by weight of a filtration aid it added in the treatment.

7. A process as claimed in claim 1, wherein an acid is added before, during or after the treatment.

8. A purified ethoxylated fatty acids obtainable by the process as claimed in claim 1.

9. In a method for the production of pharmaceutical formulations comprising preparing a solution of a pharmaceutically active compound in a solvent, the improvement wherein the solvent comprises ethoxylated fatty acids purified by the process as claimed in claim 1.

* * * * *

UNITED STATES PATENT AND TRADEMARK OFFICE
CERTIFICATE OF CORRECTION

PATENT NO.: 6,096,911

DATED: August 1, 2000

INVENTOR(S): DRALLE-VOSS et al.

It is certified that error appears in the above-identified patent and that said Letters Patent is hereby corrected as shown below:

Col. 4, claim 1, line 12, after "substance" insert a comma --,--.

Col. 4, claim 6, line 26, "aid it" should be --aid is--.

Signed and Sealed this

Seventeenth Day of April, 2001

Attest:

NICHOLAS P. GODICI

Attesting Officer     Acting Director of the United States Patent and Trademark Office